US00PP20042P2

(12) United States Plant Patent
Unger

(10) Patent No.: US PP20,042 P2
(45) Date of Patent: Jun. 2, 2009

(54) ***SALVIA* PLANT NAMED 'SAL CIS 07'**

(50) Latin Name: *Salvia leucantha*
Varietal Denomination: SAL CIS 07

(76) Inventor: Christiaan Unger, Robert Koch Strasse 7 67511, Worms (DE)

( * ) Notice: Subject to any disclaimer, the term of this patent is extended or adjusted under 35 U.S.C. 154(b) by 29 days.

(21) Appl. No.: 11/824,106

(22) Filed: Jun. 30, 2007

(51) Int. Cl.
*A01H 5/00* (2006.01)

(52) U.S. Cl. ..... Plt./475
(58) Field of Classification Search ..... Plt./475
See application file for complete search history.

*Primary Examiner*—Wendy C. Haas
(74) *Attorney, Agent, or Firm*—Mark P. Bourgeois

(57) ABSTRACT

A new and distinct *Salvia* plant cultivar is disclosed, characterized by a tall, upright, slightly mounding growth habit; dark green foliage; flocculent violet-colored flowers; and a year round flowering habit.

1 Drawing Sheet

Latin name of the genus and species: *Salvia leucantha*.
Variety denomination: 'SAL CIS 07'.

BACKGROUND OF THE INVENTION

The new cultivar is a product of open pollination in a mass selection of *Salvia* 'Violet Wonder' (not patented) in May 2002. It was discovered and selected as a single plant by Christiaan Unger in May 2003 in Rheinfelden, Germany.

Asexual reproduction of the new cultivar 'SAL CIS 07' by vegetative cuttings was performed in Oxnard, Calif., and has shown that the unique features of this cultivar are stable and reproduced true to type on successive generations.

SUMMARY OF THE INVENTION

The cultivar 'SAL CIS 07' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SAL CIS 07.' These characteristics in combination distinguish 'SAL CIS 07' as a new and distinct *Salvia* cultivar:

1. Tall, upright, slightly mounding growth habit;
2. Dark green foliage;
3. Flocculent violet-colored flowers; and
4. A year round flowering habit.

Plants of the new cultivar differ from plants of the parent 'Violet Wonder' primarily in the color and size of the foliage and inflorescences. The new cultivar has smaller leaves with a more intense color as well as smaller flowers.

In comparison to the commercially available variety 'Santa Barbara' (U.S. Plant Pat. No. 12,949), 'SAL CIS 07' has a much faster growth rate. Additionally, 'SAL CIS 07' has darker, larger foliage with more leaves per lateral branch. Finally, 'SAL CIS 07' has darker violet inflorescences that can turn very light violet in full sun.

BRIEF DESCRIPTION OF THE PHOTOGRAPH

The accompanying drawing illustrates in full color a typical plant of 'SAL CIS 07' grown in an outdoor garden. The colors are as nearly true as is reasonably possible in a color representative of this type.

DETAILED BOTANICAL DESCRIPTION

In the following description, color references are made to The Royal Horticultural Society Colour Chart except where general terms of ordinary dictionary significance are used. The following observations and measurements describe 'SAL CIS 07' plants grown in Oxnard, Calif. during the months of January through June in an outdoor garden. The growing temperature ranged from 12° C. to 15° C. at night to 12° C. to 20° C. during the day. Measurements and numerical values represent averages of typical flowering types.

Botanical classification: *Salvia hybrida* cultivar 'SAL CIS 07.'
Commercial classification: Sage.

PROPAGATION

Time to rooting: 10 to 16 days at 22° C.
Root description: Medium.

PLANT

Growth habit: Upright, slightly mounding herbaceous perennial.
Height: Approximately 72 cm.
Plant spread: Approximately 80 cm.
Growth rate: Fast.
Branching characteristics: Alternate.
Length of lateral branches: Approximately 68 cm.
Number of leaves per lateral branch: Approximately 38.
Internode length: Approximately 3 cm.
Age of plant described: Approximately 139 days.

FOLIAGE

Leaf:
*Arrangement.*—Opposite.
*Average length.*—Approximately 18.8 cm.

*Average width.*—Approximately 2.15 cm.
*Shape of blade.*—Lanceolate.
*Apex.*—Acute.
*Base.*—Rounded.
*Attachment.*—Petiolate.
*Margin.*—Crenulate.
*Texture of top surface.*—Very pubescent.
*Texture of bottom surface.*—Very pubescent.
*Color.*—Young foliage upper side. Near Green 137B. Young foliage under side: Near Green 138B. Mature foliage upper side. Near Green 137A. Mature foliage under side: Near Green 138B.
*Venation.*—Type: Reticulate. Venation color upper side: Near Grey 201A. Venation color under side: Near Grey 201A.

Petiole:
*Average length.*—Approximately 2 cm.
*Color.*—Near Grey 201A.
*Diameter.*—Approximately 0.3 cm.

FLOWER DESCRIPTION

Flowering season: Year round in Southern California and spring to summer in cooler regions of California.
Inflorescence form: Racemiform.
Flower arrangement: Whorls.
Quantity of flowers: Between 7 and 14 flowers per whorl and between 8 and 18 whorls per raceme.
Distance between whorls: Approximately 1 to 6 cm.
Flower bud:
*Shape.*—Pandurate.
*Color.*—Near Violet 86A.
*Surface.*—Flocculent.
*Color of flocculence.*—Near Purple 79D.
*Length.*—Approximately 8 mm.
*Diameter.*—Approximately 6 mm.

Corolla tube:
*Shape.*—Tubular.
*Surface.*—Flocculent.
*Color.*—Near Violet 86A.

Flower dimensions (calyx, corolla tube, and lobes):
*Length.*—Approximately 2.8 cm.
*Diameter.*—Approximately 0.4 cm.

Corolla lobes:
*Quantity.*—Two primary lobes and two reduced lateral lobes.
*Shape.*—Upper lobe falcate and lower lobe spreading.
*Color.*—Near Violet 86B.

Petals:
*Quantity: Two.*
*Color.*—Near Purple 79A with shades of Purple 78A.
*Shape.*—Petals are basally fused and spatulate.

Aspect: Drooping.
Peduncle:
*Length.*—Approximately 14 cm.
*Width.*—Approximately 0.3 cm.
*Surface.*—Flocculent.
*Color.*—Near Greyed-Green 197A.

Calyx:
*Shape.*—Tubular-shaped.
*Length.*—Approximately 0.1 cm.
*Diameter.*—Approximately 8 mm.
*Color.*—Outer surface: Near Violet 86A. Inner surface: Near Violet 86B.
*Texture.*—Flocculent.

Sepals:
*Quantity.*—Two.
*Fused or unfused.*—Basally fused.
*Color.*—Near Violet 86B.

REPRODUCTIVE ORGANS

Pistil:
*Quantity.*—One.
*Shape.*—Filiform.
*Length.*—Approximately 16 mm.
*Width.*—Approximately 0.6 mm.
*Color.*—Near Yellow-White 158D.
*Surface.*—Flocculent.

Stigma:
*Shape.*—Two-lobed.
*Length.*—Approximately 5 mm.
*Width.*—Approximately 0.6 mm.
*Color.*—Near Violet 86B.

Style:
*Shape.*—Filiform.
*Length.*—Approximately 8 mm.
*Width.*—Approximately 4 mm.
*Color.*—Near Yellow-White 158D.

Stamens:
*Quantity.*—Two.
*Length.*—Approximately 4 mm.
*Width.*—Approximately 1.1 mm.
*Color.*—Near Yellow-White 158D.

Anther:
*Length.*—Approximately 2.2 mm.
*Width.*—Approximately 1.2 mm.
*Color.*—Near Yellow-White 158A. No pollen has been observed on this variety.

Ovary:
*Length.*—Approximately 2 mm.
*Width.*—Approximately 1 mm.
*Color.*—Near Yellow-White 158D.

OTHER CHARACTERISTICS

Disease resistance: Neither resistance nor susceptibility to diseases or pests has been observed in this variety.
Drought tolerance/cold tolerance: Plants are moderately drought tolerant. The new cultivar can tolerate temperatures from −10 to 40° C.
Fruit/seed production: Not observed because commercially the plants are discarded or the flowers removed before seed set occurs.

What is claimed is:

1. A new and distinct cultivar of *Salvia* plant named ‘SAL CIS 07’ as herein illustrated and described.

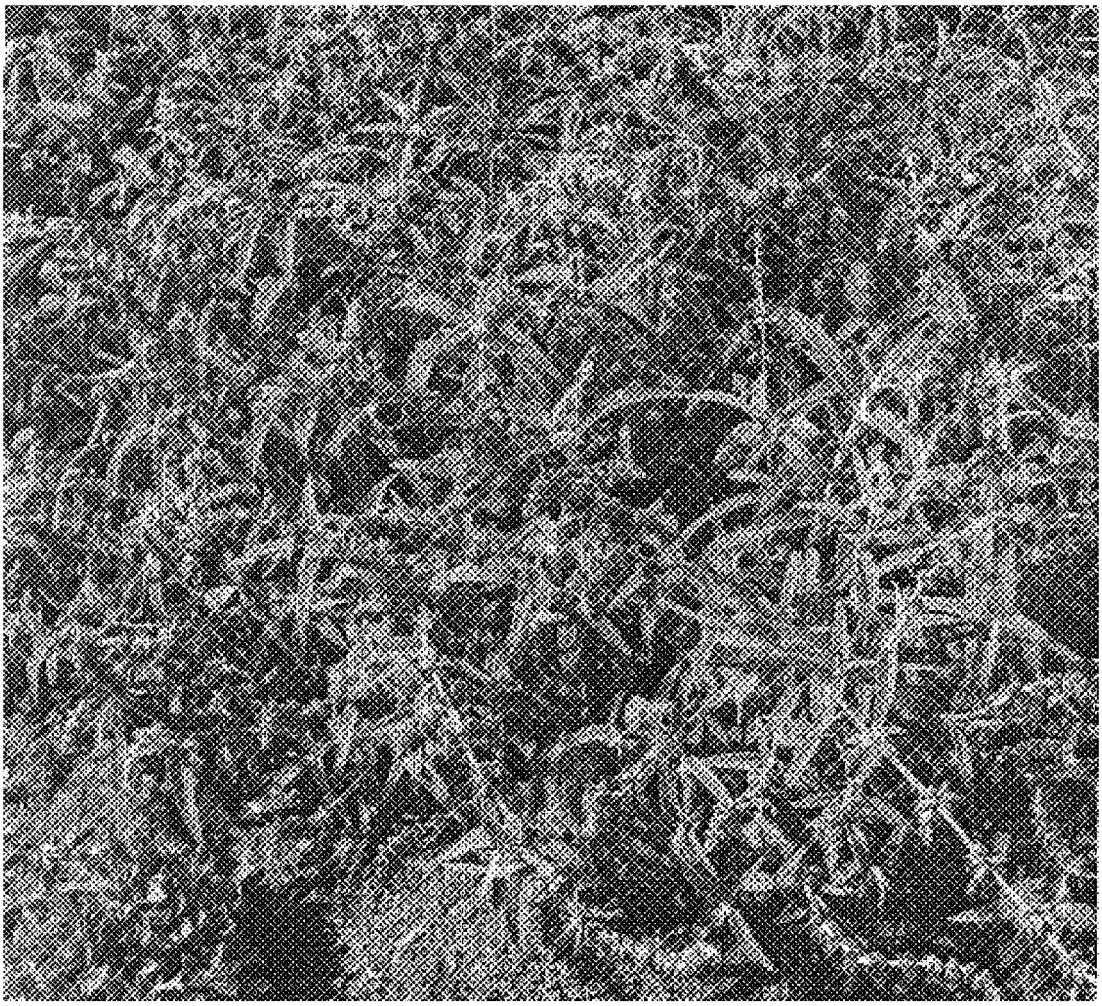

* * * * *